United States Patent [19]
Zeng et al.

[11] Patent Number: 6,051,626
[45] Date of Patent: *Apr. 18, 2000

[54] ADHESIVE COMPOSITION FOR DENTAL OR SURGICAL TREATMENT

[75] Inventors: Weiping Zeng; Akari Shimozono; Tsuyoshi Banba, all of Moriyama, Japan

[73] Assignee: Sun Medical Co., Ltd., Moriyama, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/946,703

[22] Filed: Oct. 8, 1997

[30] Foreign Application Priority Data

Oct. 11, 1996 [JP] Japan ................................. 8-269743

[51] Int. Cl.⁷ ........................... A61K 6/083; A61K 6/00; C08K 5/55

[52] U.S. Cl. ........................... 523/118; 523/116; 522/47; 522/64; 524/183; 524/357; 526/196

[58] Field of Search ................................. 523/176, 118; 522/47, 64; 524/183, 357; 526/196

[56] References Cited

U.S. PATENT DOCUMENTS

| | | | |
|---|---|---|---|
| 4,222,835 | 9/1980 | Dixon | 428/251 |
| 4,259,117 | 3/1981 | Yamauchi et al. | 523/116 |
| 4,985,516 | 1/1991 | Sakashita et al. | 526/196 |
| 5,228,907 | 7/1993 | Eppinger et al. | 523/116 |
| 5,264,513 | 11/1993 | Ikemura et al. | 523/118 |
| 5,281,641 | 1/1994 | Nishimura et al. | 523/116 |
| 5,530,038 | 6/1996 | Yamamoto et al. | 523/118 |

FOREIGN PATENT DOCUMENTS

| | | |
|---|---|---|
| 0348166 | 12/1989 | European Pat. Off. . |
| 0684033 | 11/1995 | European Pat. Off. . |
| 0684034 | 11/1995 | European Pat. Off. . |
| 7-97306 | 4/1995 | Japan . |

*Primary Examiner*—Andrew E. C. Merriam
*Attorney, Agent, or Firm*—Sherman and Shalloway

[57] ABSTRACT

An adhesive composition for dental or surgical treatment comprising (A) 2 to 24 parts by weight of an organic boron compound, (B) 0.002 to 0.5 part by weight of a photopolymerization initiator, (C) 75 to 97 parts by weight of a polymerizable monomer mixture comprising 2 to 20% by weight of a monomer containing an acidic group and 80 to 98% by weight of a monomer containing no acidic group, and (D) optionally, 250 parts or less by weight of a filler.

12 Claims, No Drawings

ADHESIVE COMPOSITION FOR DENTAL OR SURGICAL TREATMENT

DETAILED DESCRIPTION OF THE INVENTION

This invention relates to an adhesive composition for dental or surgical treatment. More specifically, it relates to an adhesive composition for dental or surgical treatment, which is capable of controlling cure rate and which has improved operability and excellent adhesion performance and treatment effect.

In the fields of dental treatment and surgical treatment, it is required to firmly bond together a restoration material and a tooth or hard tissue, and there have already been proposed various adhesive compositions to be used for this purpose. It is confirmed by clinical results for a prolonged period of time that adhesive compositions comprising tributyl boron and a partial oxide thereof as a polymerization initiator, among the conventionally known adhesive compositions, have excellent adhesion performance and are little harmful to living bodies.

Although the above adhesive compositions comprising tributyl boron and a partial oxide thereof as a polymerization initiator have excellent performance, their cure rates are relatively low and it takes a long time for them to exhibit sufficient adhesion performance. Therefore, their operating performance has been desired to be further improved.

JP-A 7-97306 (the term "JP-A" as used herein means an "unexamined published Japanese patent application") discloses at least one member selected from the group consisting of organic peroxides, inorganic peroxides, alkyl borane, partial oxides of alkyl borane, α-diketones, organic amines, organic sulfinic acids, inorganic sulfur compounds and barbituric acids, but fails to disclose a polymerization initiator comprising an organic boron compound and a photopolymerization initiator in a specific ratio, and its effect.

It is an object of the present invention to provide an adhesive composition for dental or surgical treatment, which has excellent operability, adhesion performance and treatment effect in bonding between a restoration material and a tooth or other hard tissue of living bodies.

It is another object of the present invention to provide an adhesive composition for dental or surgical treatment, which is capable of controlling a cure rate while retaining the above properties of the adhesive composition.

Other objects and advantages of the present invention will become apparent from the following description.

Surprisingly, the inventors of the present invention have found that the above objects can be attained by using an adhesive composition containing a polymerization initiator comprising an organic boron compound and an appropriately small amount of a photopolymerization initiator. Thus, the present invention has been accomplished.

According to the present invention, the above objects and advantages of the present invention can be attained by an adhesive composition for dental or surgical treatment comprising:

(A) 2 to 24 parts by weight of an organic boron compound;

(B) 0.002 to 0.5 part by weight of a photopolymerization initiator; and (C) 75 to 97 parts by weight of a polymerizable monomer mixture which comprises 2 to 20% by weight of a monomer containing an acidic group and 80 to 98% by weight of a monomer containing no acidic group, the total of components (A), (B) and (C) being 100 parts by weight.

In the adhesive composition of the present invention, the organic boron compound as the component (A) is an organic boron polymerization initiator. Illustrative examples of the organic boron compound as the component (A) include trialkyl boron such as triethyl boron, tripropyl boron, triisopropyl boron, tributyl boron, tri-sec-butyl boron, triisobutyl boron, tripentyl boron, trihexyl boron, trioctyl boron, tridecyl boron, tridodecyl boron, tricyclopentyl boron, tricyclohexyl boron or the like: alkoxyalkyl boron such as butoxydibutyl boron or the like; dialkyl borane such as butyldicyclohexyl borane, diisoamyl borane, 9-borabicyclo[3.3.1]nonane or the like; partially oxidized trialkyl boron such as partially oxidized tributyl boron or the like. Of these, trialkyl borane and partial oxides thereof are preferred. Above all, when tributyl boron or partially oxidized tributyl boron is used, a particularly favorable result can be obtained. The most preferred organic boron compound is partially oxidized tributyl boron.

The partially oxidized trialkyl boron is obtained by adding 0.3 to 0.9 mole of oxygen to 1 mole of trialkyl boron.

In the adhesive composition of the present invention, the component (B) is a photopolymerization initiator. Any photopolymerization initiator can be used as the photopolymerization initiator (B) without restriction if it can initiate polymerization of a polymerizable monomer by irradiation using a visible or ultraviolet light. The photopolymerization initiator is a visible or ultraviolet light sensitizer exemplified by benzoins such as benzoin, benzoin methylether, benzoin ethylether and benzoin isopropyl ether; α-diketones such as benzyl, 4,4'-dichlorobenzyl, diacetyl, α-cyclohexanedione, d,l-camphorquione (CQ), camphorquinone-10-sulfonic acid and camphorquinone-10-carboxylic acid; diphenyl monoketones such as benzophenone, benzoyl methyl benzoate and hydroxybenzophenone; thioxantones such as 2,4-diethyl thioxantone and 2-isopropyl thioxantone; acylphosphine oxides such as 2,4,6-trimethyl benzoyldiphenyl phosphine oxide; and the like. These photopolymerization initiators may be used alone or in combination. Of these, α-dikentones such as 4,4'-dichlorobenzyl, diacetyl, α-cyclohexanedione, d,l-camphorquinone (CQ), camphorquinone-10-sulfonic acid, camphorquinone-10-carboxylic acid, and acylphosphine oxides are preferred. Particularly preferred are d,l-camphorquinone and camphorquinone-10-carboxylic acid, because a favorable result can be obtained.

To improve the polymerization initiation effect of the above photopolymerization initiators, there can be used a reducing compound which does not exert an adverse influence on the catalytic effect of an organic boron compound. Illustrative examples thereof include organic reducing compounds such as N,N-dimethylaniline, N,N-dimethyl-p-toluidine, N,N-diethyl-p-toluidine, N,N-diethanol-p-toluidine, N,N-dimethyl-p-tert-butylaniline, N,N-dimethylanisidine, N,N-dimethyl-p-chloroaniline, N,N-dimethylaminoethyl (meth)acrylate, N,N-diethylaminoethyl (meth)acrylate, N,N-dimethylaminobenzoic acid and alkyl esters thereof, N,N-diethylaminobenzoic acid and alkyl esters thereof, N,N-dimethylaminobenzaldehyde, N-phenylglycine, N-triglycine, N,N-(3-methacryloyloxy-2-hydroxypropyl)phenyl glycine and the like.

The amount of the above reducing compound is generally in the range of 0.5 to 2.0 times the amount (weight) of the photopolymerization initiator used.

In the adhesive composition of the present invention, the component (C) is a polymerizable monomer mixture. The polymerizable monomer mixture comprises 2 to 20% by weight of a monomer containing an acidic group and 80 to 98% by weight of a monomer containing no acidic group.

The monomer containing no acidic group is not limited to a particular one, and generally known monofunctional monomers and polyfunctional monomers may be used. (Meth) acrylate-based monomers having relatively low stimulus to human bodies are particularly preferred.

Illustrative examples of the monofunctional monomer contained in the component (C) include alkyl (meth) acrylates such as methyl (meth)acrylate, ethyl (meth)acrylate, propyl (meth)acrylate, butyl (meth)acrylate, hexyl (meth)acrylate, 2-ethylhexyl (meth)acrylate, dodecyl (meth) acrylate, lauryl (meth)acrylate, cyclohexyl (meth)acrylate, benzyl (meth)acrylate and isobornyl (meth)acrylate; hydroxyalkyl esters of (meth)acrylic acid such as 2-hydroxyethyl (meth)acrylate, 2- or 3-hydroxypropyl (meth)acrylate, 4-hydroxybutyl (meth)acrylate, 5-hydroxypentyl (meth)acrylate, 6-hydroxyhexyl (meth) acrylate, 1,2- or 1,3-dihydroxypropyl mono (meth) acrylate and erythritol mono (meth) acrylate; polyethylene glycol mono(meth)acrylates such as diethylene glycol mono(meth) acrylate, triethylene glycol mono(meth)acrylate, polyethylene glycol mono(meth)acrylate and polypropylene glycol mono(meth)acrylate; (poly)glycol monoalkyl ether (meth) acrylates such as ethylene glycol monomethylether (meth)acrylate, ethylene glycol monoethylether (meth)acrylate, diethylene glycol monomethylether (meth)acrylate, triethylene glycol monomethylether (meth)acrylate, polyethylene glycol monomethylether (meth)acrylate and polypropylene glycol monoalkylether (meth)acrylate; fluoroalkyl esters of (meth)acrylic acid such as perfluorooctyl (meth)acrylate and hexafluorobutyl (meth)acrylate; silane compounds having a (meth)acryloxyalkyl group such as γ-(meth)acryloxypropyl trimethoxysilane and γ-(meth)acryloxypropyltri(trimethylsiloxy)silane; (meth)acrylates having a hetero ring such as tetrafurfuryl (meth)acrylate; and the like.

Illustrative examples of the polyfunctional monomer contained in the component (C) include alkane polyol poly (meth)acrylates such as ethylene glycol di(meth)acrylate, propylene glycol di(meth)acrylate, butylene glycol di(meth) acrylate, neopentyl glycol di(meth)acrylate, hexylene glycol di(meth)acrylate, trimethylolpropane tri(meth)acrylate and pentaerythritol tetra(meth)acrylate; polyoxyalkane polyol poly(meth)acrylates such as diethylene glycol di(meth) acrylate, triethylene glycol di(meth)acrylate, polyethylene glycol di(meth)acrylate, dipropylene glycol di(meth) acrylate, polypropylene glycol di(meth)acrylate, dibutylene glycol di(meth)acrylate and dipentaerythritol hexa(meth) acrylate; aliphatic or aromatic di(meth)acrylates represented by the following formula:

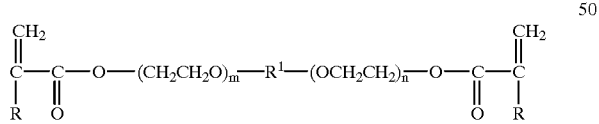

wherein R is a hydrogen atom or a methyl group, m and n are each 0 or a positive number, and $R^1$ is

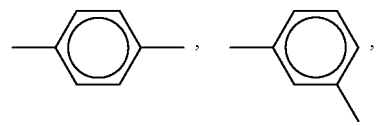

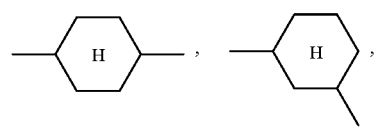

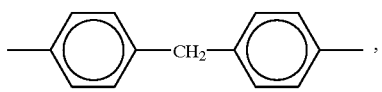

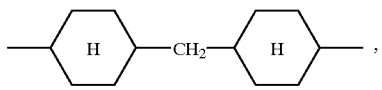

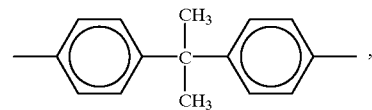

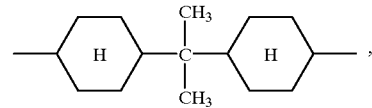

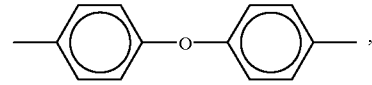

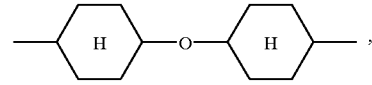

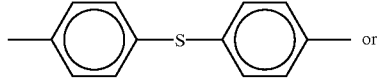

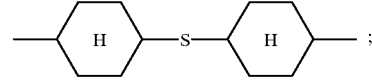

aliphatic and aromatic epoxy di(meth)acrylates represented by the following formula:

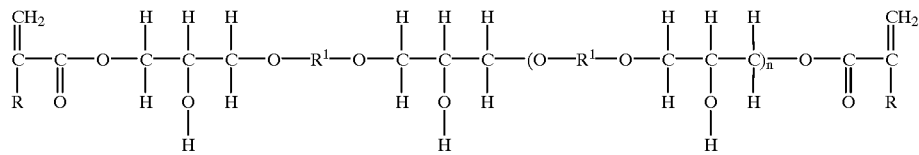

wherein R is a hydrogen atom or a methyl group, n is 0 or a positive number, and $R^1$ is —(CH$_2$)$_2$—, —(CH$_2$)$_4$—,

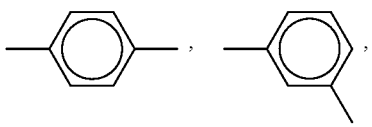

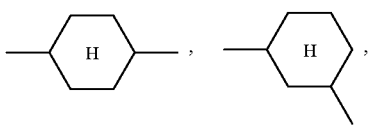

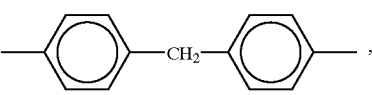

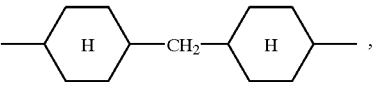

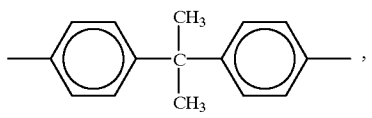

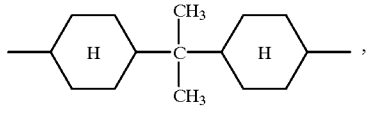

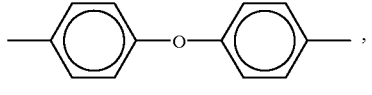

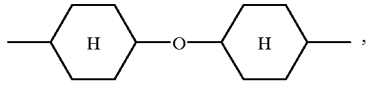

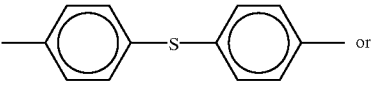

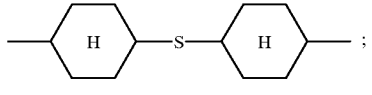

polyfunctional (meth)acrylates having an urethane bond in the molecule represented by the following formula:

wherein R is a hydrogen atom or a methyl group, and $R^1$ is —(CH$_2$)$_2$—, —(CH$_2$)$_4$—, —(CH$_2$)$_6$—,

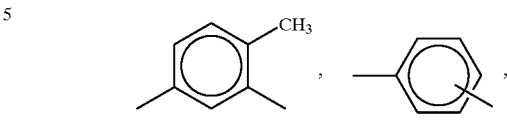

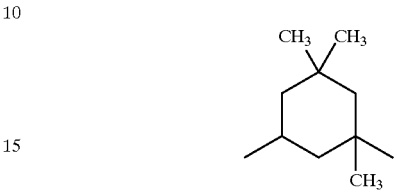

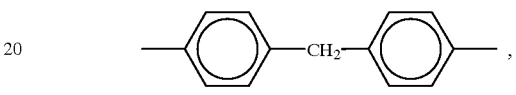

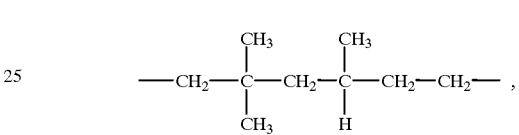

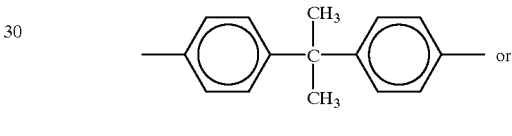

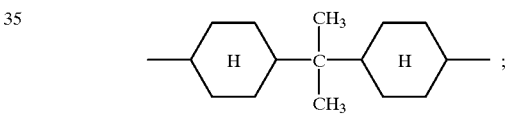

and the like.

Of these, the particularly preferable monofunctional polymerizable monomer is an alkyl (meth)acrylate such as methyl (meth)acrylate or ethyl (meth)acrylate; a (meth)acrylate containing a hydroxyl group such as 2-hydroxyethyl (meth)acrylate, 1,3-dihydroxypropyl mono(meth)acrylate or erythritol mono(meth)acrylate; or a (meth)acrylate having an ethylene glycol chain in the molecule such as triethylene glycol monomethylether (meth)acrylate or triethylene glycol mono(meth)acrylate. And, the particularly preferable polyfunctional polymerizable monomer is a di(meth)acrylate having an ethylene glycol chain in the molecule such as triethylene glycol di(meth)acrylate or polyethylene glycol di(meth)acrylate; a compound represented by the following formula:

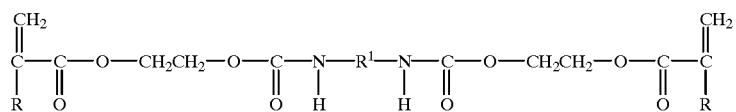

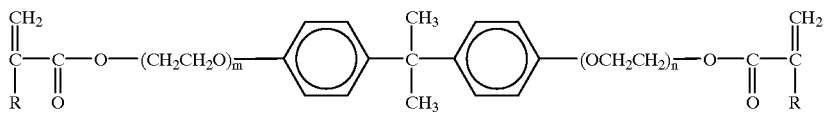

wherein R is a hydrogen atom or a methyl group and m+n is 2 to 20; a compound represented by the following formula:

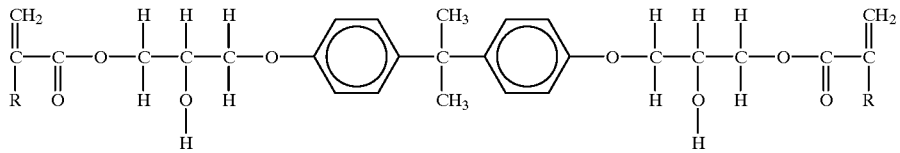

wherein R is a hydrogen atom or a methyl group; a compound represented by the following formula:

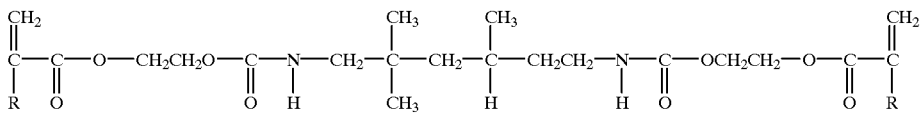

wherein R is a hydrogen atom or a methyl group; or the like.

These monofunctional polymerizable monomers and polyfunctional polymerizable monomers may be used alone or in admixture of two or more.

The acidic group-containing polymerizable monomer contained in the component (C) is preferably a polymerizable monomer having a carboxylic acid group, carboxylic anhydride group, phosphoric acid group or sulfonic acid group. Illustrative examples of the acidic group-containing monomer include monomers containing a carboxylic acid group or a carboxylic anhydride group such as (meth)acrylic acid and anhydride thereof, 1,4-di(meth)acryloxyethylpyromellitic acid, 6-(meth)acryloxyethylnaphthalene-1,2,6-tricarboxylic acid, N-(meth)acryloyl-p-aminobenzoic acid, N-(meth)acryloyl-o-aminobenzoic acid, N-(meth)acryloyl-m-aminobenzoic acid, N-(meth)acryloyl-5-aminosalicylic acid, N-(meth)acryloyl-4-aminosalicylic acid, 4-(meth)acryloxyethyltrimellitic acid and anhydride thereof, 4-(meth)acryloxybutyltrimellitic acid and anhydride thereof, 4-(meth)acryloxyhexyltrimellitic acid and anhydride thereof, 4-(meth)acryloxydodecyltrimellitic acid and anhydride thereof, 2-(meth)acryloyloxybenzoic acid, 3-(meth)acryloyloxybenzoic acid, 4-(meth)acryloyoxybenzoic acid, β-(meth)acryloyloxyethyl hydrogen succinate, β-(meth)acryloyloxyethyl hydrogen maleate, β-(meth)acryloyloxyethyl hydrogen phthalate, 11-(meth)acryloyloxy-1,1-undecanedicarboxylic acid, and p-vinylbenzoic acid; monomers containing a phosphoric acid group such as (2-(meth)acryloxyethyl)phosphoric acid, (2-(meth)acryloxyethylphenyl)phosphoric acid and 10-(meth)acryloxydecylphosphoric acid; and monomers containing a sulfonic acid group such as p-styrenesulfonic acid and 2-acrylamide-2-methylpropanesulfonic acid.

These acidic group-containing polymerizable monomers may be used alone or in combination. The acidic group-containing polymerizable monomer is preferably used in an amount of 2 to 20 parts by weight based on 100 parts by weight of the total of the whole polymerizable monomer components.

In the composition of the present invention, the component (A) is used in an amount of 2 to 24 parts by weight, preferably 3 to 20 parts by weight, the component (B) 0.002 to 0.5 part by weight, preferably 0.003 to 0.4 part by weight and the component (C) 75 to 97 parts by weight, preferably 80 to 95 parts by weight, based on 100 parts by weight of the total of the components (A), (B) and (C).

The photopolymerization initiator (B) is preferably used in an amount of 0.1 to 2 parts by weight, more preferably 0.2 to 1 part by weight, based on 100 parts by weight of the total of the organic boron compound (A) and the photopolymerization initiator (B). When the content of the photopolymerization initiator is less than 0.1 part by weight, a composition is difficult to obtain the expected effect on controlling the polymerization rate, while when the proportion is more than 2 parts by weight, the contribution of the photopolymerization initiator to the curing of a composition through a polymerization reaction becomes larger than the contribution of the organic boron compound, and hence, it may be difficult to obtain sufficient adhesion performance in some cases.

The adhesive composition of the present invention can contain a component (D). The component (D) is a filler which may be a generally known inorganic filler, organic filler or organic.inorganic composite filler.

Illustrative examples of the inorganic filler include metal oxides such as zirconium oxide, bismuth oxide, titanium oxide, zinc oxide and aluminum oxide; metal salts such as calcium carbonate, bismuth carbonate, calcium phosphate, zirconium phosphate and rodium sulfate; and glass fillers such as silica glass, rodium-containing glass, strontium-containing glass and zirconia silicate glass. These inorganic fillers may be used alone or in combination.

To achieve firm bonding between an inorganic filler and a resin, it is advisable to use the above fillers subjected to a surface treatment such as a silane treatment or a polymer coating.

Illustrative examples of the organic filler include organic metal compounds such as organic bismuth compounds, organic zirconium compounds and organic titanium compounds or the like; non-crosslinkable polymers such as polyvinyl acetate, polymethyl (meth)acrylate, polyethyl (meth)acrylate, methyl (meth)acrylate-butyl (meth)acrylate copolymer, polystyrene, polyvinyl chloride, ethylene-vinyl acetate copolymer, (meth)acrylic acid-MMA copolymer, (meth)acrylic acid-styrene copolymer, maleic acid (anhydride)-MMA copolymer, maleic acid (anhydride)-styrene copolymer, methyl (meth)acrylate-ethyl (meth) acrylate copolymer and methyl (meth)acrylate-styrene copolymer or the like; and organic polymers such as methyl (meth)acrylate-ethylene glycol di(meth)acrylate copolymer, methyl (meth)acrylate-triethylene glycol di(meth)acrylate copolymer, butadiene-based crosslinkable polymers and polyfunctional (meth)acrylic crosslinkable polymers or the like. These organic fillers may be used alone or in combination.

Further, organic.inorganic composite fillers containing the above inorganic fillers and/or the above organic fillers can be used.

These inorganic fillers, organic fillers and organic.inorganic composite fillers may be used alone or in combination.

The adhesive composition of the present invention may contain the filler (D) in an amount of 250 parts or less by weight based on 100 parts by weight of the total of the components (A), (B) and (C). Preferably, the filler (D) is composed of an organic polymer and contained in an amount of 3 to 100 parts by weight.

As another preferable aspect, the filler (D) may be an inorganic filler or organic.inorganic composite filler and contained in an amount of 10 to 250 parts by weight. Further, when the filler is a combination of an organic filler and an inorganic filler or organic.inorganic composite filler, it preferably comprises 50 to 100 parts by weight of an organic filler and 50 to 150 parts by weight of at least one member selected from the group consisting of inorganic fillers and organic.inorganic composite fillers.

According to a first preferred aspect of the present invention, there is provided an adhesive composition comprising 2 to 20 parts by weight of an organic boron compound (A), 0.002 to 0.5 part by weight of a photopolymerization initiator (B), 80 to 97 parts by weight of a polymerizable monomer mixture (C) and 10 to 250 parts by weight of at least one filler (D) selected from the group consisting of inorganic fillers and organic.inorganic composite fillers, the total of the components (A), (B) and (C) being 100 parts by weight, and the proportion of the component (D) being based on 100 parts by weight of the total of the components (A), (B) and (C).

According to a second preferred aspect of the present invention, there is provided an adhesive composition comprising 2 to 20 parts by weight of an organic boron compound (A), 0.002 to 0.5 part by weight of a photopolymerization initiator (B), 80 to 97 parts by weight of a polymerizable monomer mixture (C), and fillers (D) which are a combination of 50 to 100 parts by weight of an organic polymer filler and 50 to 150 parts by weight of at least one filler selected from the group consisting of inorganic fillers and organic.inorganic composite fillers, the total of the components (A), (B) and (C) being 100 parts by weight and the proportion of the component (D) being based on 100 parts by weight of the components (A), (B) and (C).

The adhesive composition of the present invention may contain a solvent, colorant and polymerization inhibitor such as hydroquinone in suitable amounts as required.

To improve the safety of the organic boron compound, in particular, the adhesive composition of the present invention may contain a solvent, a filling material and the like in suitable amounts as required.

To maintain storage stability, the adhesive composition of the present invention is preferably prepared by dividing the components of a combination of the components (A), (B) and (C) or the components of a combination of (A), (B), (C) and (D) into at least two groups for preservation, and mixing these components before use.

Prior to the dental or surgical treatment using the adhesive composition of the present invention, a pretreatment is preferably made on the tooth or hard tissue. The pretreatment is, for example, an etching of the adhesion surface with an acidic solution, a modification of the adhesion surface with a primer, the etching and modification of the adhesion surface with a primer having etching capability, or the like. The acidic solution is, for example, an aqueous solution containing 5 to 60% by weight of phosphoric acid or an aqueous solution containing 10% by weight of citric acid and 3% by weight of ferric chloride. The primer for modifying a dental surface is, for example, an aqueous solution containing 20 to 50% by weight of 2-hydroxyethyl (meth)acrylate or 1,3-dihydroxypropyl mono(meth)acrylate. The primer having etching capability is, for example, an aqueous solution containing a monomer having an organic acid or acidic group and a component for modifying a demineralized tooth to promote the diffusion of an adhesive into tooth. Illustrative examples of the component for modifying a tooth to promote the diffusion of an adhesive into tooth include monomers having a hydroxyl group such as (poly) alkylene glycol, 2-hydroxyethyl (meth)acrylate and 1,3-dihydroxypropyl mono(meth)acrylate and polyethylene glycol (meth)acrylate.

To further illustrate the present invention, the following Examples are given, but the present invention shall not be limited to these Examples.

The following abbreviations stand for the following compounds.

MMA: methyl methacrylate (a special grade, a product of Wako Pure Chemical Industries, Ltd.)

2.6E: 2,2-bis(4-methacryloxyethoxyphenyl)propane

HEMA: 2-hydroxyethyl methacrylate

4-META: 4-methacryloxyethyl trimellitic anhydride (a product of Sun Medical Co. Ltd.)

TBB.O: partially oxidized tributyl boron (a product of Sun Medical Co. Ltd.)

p-MBS: methyl methacrylate-butadiene-styrene copolymer p-MMA: polymethyl methacrylate powders (molecular weight of 400,000, particle diameter of 25 $\mu$m, a product of Sun Medical Co. Ltd)

CQ: camphorquinone

Examples 1 to 5 (evaluation of cure rate)

Predetermined amounts of each of components shown in Table 1 were mixed at a room temperature of about 25° C., and the resulting mixture was applied to a slide glass, left to stand for 20 seconds, covered with another slide glass crosswise and irradiated with light using a visible light illuminator for dental treatment (Translux, a product of Kultzer) from above the slide glasses. The two slide glasses were softly moved at intervals of 20 seconds and the time elapsed from the time of application to the time when the two slide glasses could not move relative to each other was measured as cure time. The results are shown in Table 1.

Comparative Examples 1 to 4

The same operation as in Examples 1 to 5 was repeated except irradiation with light was omitted. The results are shown in Table 1.

TABLE 1

|  | Composition of adhesive composition (parts by weight) | Irradiation time (second) | Cure (second) |
|---|---|---|---|
| Ex. 1 | MMA:50, 2.6E:30, HEMA:10, | 10 | 90 |
| Comp. Ex. 1 | 4-META:10, TBB · 0:15, CQ:0.1 | 0 | 120 |
| Ex. 2 | MMA:44, 2.6E:26, HEMA:15, pMBS:5, | 10 | 120 |
| Comp. Ex. 2 | pMMA:3, 4-META:8, TBB · 0:15, CQ:0.1 | 0 | 160 |
| Ex. 3 | MMA:44, 2.6E:25, HEMA:15, pMBS:5, | 10 | 120 |
| Comp. Ex. 3 | pMMA:3, 4-META:8, TBB · 0:15, CQ:0.2 | 0 | 170 |
| Ex. 4 | MMA:42, 2.6E:30, HEMA:15, pMBS:5, | 10 | 110 |
| Comp. Ex. 4 | 4-META:8, TBB · 0:15, CQ:0.1 | 0 | 150 |
| Ex. 5 | MMA:47, 4-META:3, pMMA:50, | 40 | 350 |
| Comp. Ex. 5 | TBB · 0:5, CQ:0.05 | 0 | 440 |

Ex.: Example, Comp. Ex.: Comparative Example

Examples 6 and 7 (evaluation of adhesion performance—sealability at the time of filling adhesive in cavity of tooth)

A lip side surface of a bovine front tooth was cut out to expose dentin, the dentin surface was burnished with a No. 1000 emery paper and finished, and a round cavity having a diameter of 3 to 4 mm and a depth of 1 to 1.5 mm was formed with a hand piece in the direction perpendicular to the finished surface.

The formed cavity was pretreated with an etching solution comprising 3% of ferric chloride and 10% of citric acid for 10 second, washed with water for 20 seconds and dried with an air blow for 15 seconds. Thereafter, a composition shown in Table 2 was applied to the cavity, and a coating of the adhesive composition was uniformly spread out by a slight air blowing and left to stand for about 20 seconds. The composition was irradiated with light using a visible light illuminator for dental treatment (Translux, a product of Kultzer) for 10 seconds. Subsequently, a composite resin for dental treatment (Herculite, a product of Kerr) was filled in the cavity and irradiated with visible light using the above visible light illuminator for dental treatment for 40 seconds to cure the composite resin.

The surface of the cavity filled with the composite resin was burnished with a No. 1000 emery paper and the presence of a gap between the filled material at the cavity margin and the cavity wall was observed through an electron microscope.

(The length of adhesive interface without a gap)/(total length of adhesive interface)×10 is taken as sealability representing adhesion performance. The results are shown in Table 2. The larger the numeral value the better the adhesion performance is.

Comparative Examples 6 and 7

The same operation as in Examples 6 and 7 was repeated except irradiation with light was omitted. The results are shown in Table 2.

TABLE 2

|  | Composition of adhesive composition (parts by weight) | Cavity marginal adaption score | Cavity wall adaption score |
|---|---|---|---|
| Ex. 6 | MMA:42, 2.6E:30, HEMA:15, pMBS:5, | 8 | 9 |
| Comp. Ex. 6 | 4-META:8, TBB · 0:15, CQ:0.1 | 6 | 8 |
| Ex. 7 | MMA:40, 2.6E:30, HEMA:20, pMBS:5, | 8 | 9 |
| Comp. Ex. 7 | 4-META:6, TBB · 0:15, CQ:0.1 | 5 | 7 |

Ex.: Example, Comp. Ex.: Comparative Example

Examples 8 and 9 (evaluation of adhesion performance—adhesion strength)

A lip side surface of a bovine front tooth was cut out to expose dentin surface (or enamel surface), and the dentin (or enamel) surface was burnished with a No. 600 emery paper to form an adhesion surface.

The adhesion surface was washed with water, dried, treated with an etching solution containing 3% of ferric chloride and 10% of citric acid for 10 seconds (or 30 seconds for enamel surface), washed with water for 20 seconds and dried with an air blow for 15 seconds. Thereafter, a cellophane tape having a 5 mm-diameter circular hole was affixed to the adhesion surface to define an adhesive area.

The adhesive composition of the present invention shown in Table 3 was applied to the adhesion surface having a defined area, and a coating of the adhesive composition was uniformly spread out by a slight air blowing and left to stand for about 20 seconds, and then, irradiated with light using a visible light illuminator for dental treatment (Translux, a product of Kultzer) from a distance of 5 mm for 10 seconds. A 2 mm-thick plastic mold having a 5 mm-diameter circular hole was affixed to the adhesion surface of the coating layer and a composite resin for dental treatment (Herculite of Kerr Co.) was filled in the hole and irradiated with light using the above visible light illuminator for dental treatment from a distance of 5 mm for 40 seconds to cure the composite resin. A PMMA rod is bonded onto the cured composite resin using an adhesive for dental treatment (Superbond, a product of Sun Medical Co. Ltd) to prepare an adhesion test sample.

After the adhesion test sample was left at room temperature for 30 minutes and immersed in distilled water at 37° C. for 24 hours, a tensile test was conducted on the sample to measure adhesion strength between the acryl rod and tooth. The adhesion strength is an average of measurement values of five test samples.

The adhesion strength measured as described above is shown in Table 3.

Comparative Examples 8 and 9

The same operation as in Examples 8 and 9 was repeated except that irradiation with light was omitted and a composite resin was filled in the hole after the adhesive composition coating was left to stand for about 60 seconds. The results are shown in Table 3.

TABLE 3

| | Composition of adhesive composition (parts by weight) | Adhesion strength (MPa) |
|---|---|---|
| Ex. 8 | MMA:42, 2.6E:30, HEMA:15, pMBS:5, | 10.0 ± 4.0 |
| Comp. Ex. 8 | 4-META:8, TBB · 0:15, CQ:0.1 | 9.0 ± 3.0 |
| Ex. 9 | MMA:40, 2.6E:30, HEMA:20, pMBS:5, | 10.3 ± 3.7 |
| Comp. Ex. 9 | 4-META:6, TBB· 0:15, CQ:0.1 | 10.7 ± 4.5 |

Ex.: Example, Comp. Ex.: Comparative Example

An adhesive composition for dental or surgical treatment, which has improved operability and excellent adhesion performance and treatment effect, is obtained by using the adhesive composition of the present invention containing a polymerization initiator comprising an organic boron compound and a suitably small amount of a photopolymerization initiator.

What is claimed is:

1. An adhesive composition for dental or surgical treatment comprising:
   (A) 2 to 24 parts by weight of an organic boron compound;
   (B) 0.002 to 0.5 part by weight of a photopolymerization initiator, so that said photopolymerization initiator is present in an amount of 0.1 to 2 parts by weight, based on 100 parts by weight of the total of said organic boron compound and said photopolymerization initiator; and
   (C) 75 to 97 parts by weight of a polymerizable monomer mixture comprising 2 to 20% by weight of a monomer containing an acidic group and 80 to 98% by weight of a monomer containing no acidic group, the total of the components (A), (B) and (C) being 100 parts by weight.

2. The adhesive composition of claim 1 which further comprises 250 parts or less by weight of a filler (D) based on 100 parts by weight of the total of the components (A), (B) and (C).

3. The adhesive composition of claim 1, wherein the organic boron compound (A) is trialkyl borane and/or a partial oxide thereof.

4. The adhesive composition of claim 1, wherein the photopolymerization initiator (B) is an α-diketone or acylphosphine oxide.

5. The adhesive composition of claim 1, wherein the acidic group-containing monomer of the polymerizable monomer mixture (C) is a monomer containing an acidic group selected from the group consisting of carboxylic acid group, carboxylic anhydride group, sulfonic acid group and phosphoric acid group.

6. The adhesive composition of claim 1, wherein the monomer containing no acidic group of the polymerizable monomer mixture (C) is (meth)acrylate.

7. The adhesive composition of claim 2, wherein the filler (D) is an organic polymer and is contained in an amount of 3 to 100 parts by weight.

8. The adhesive composition of claim 2, wherein the filler (D) is an inorganic filler or organic.inorganic composite filler and is contained in an amount of 10 to 250 parts by weight.

9. The adhesive composition of claim 2, wherein the filler (D) is a combination of 50 to 100 parts by weight of an organic filler and 50 to 150 parts by weight of at least one filler selected from the group consisting of inorganic fillers and organic.inorganic composite fillers.

10. The adhesive composition of claim 2 comprising 2 to 20 parts by weight of the organic boron compound (A), 0.002 to 0.4 part by weight of the photopolymerization initiator (B), 80 to 97 parts by weight of the polymerizable monomer mixture, and 10 to 250 parts by weight of at least one filler (D) selected from the group consisting of inorganic fillers and organic.inorganic composite fillers, the total of the components (A), (B) and (C) being 100 parts by weight and the proportion of the component (D) being based on 100 parts by weight of the total of the components (A), (B) and (C).

11. The adhesive composition of claim 2 comprising 2 to 20 parts by weight of the organic boron compound (A), 0.002 to 0.4 part by weight of the photopolymerization initiator (B), 80 to 97 parts by weight of the polymerizable monomer mixture (C), and fillers (D) of a combination of 50 to 100 parts by weight of an organic polymer filler and 50 to 150 parts by weight of at least one filler selected from the group consisting of inorganic fillers and organic.inorganic composite fillers, the total of the components (A), (B) and (C) being 100 parts by weight and the proportion of the combination (D) being based on 100 parts by weight of the total of the components (A), (B) and (C).

12. A method of preparing an adhesive composition comprising
   (A) 2 to 24 parts by weight of an organic boron compound;
   (B) 0.002 to 0.5 part by weight of a photopolymerization initiator, so that said photopolymerization initiator is present in an amount of 0.1 to 2 parts by weight, based on 100 parts by weight of the total of said organic boron compound and said photopolymerization initiator, and
   (C) 75 to 97 parts by weight of a polymerizable monomer mixture comprising 2 to 20% by weight of a monomer containing an acidic group and 80 to 98% by weight of a monomer containing no acidic group,
   the total of the components (A), (B) and (C) being 100 parts by weight,
   the method comprising:
      dividing the components of a combination of the components (A), (B) and (C) into at least two groups for preservation; and
      mixing these groups of components before use.

* * * * *